United States Patent
Gan et al.

(10) Patent No.: US 11,953,593 B2
(45) Date of Patent: Apr. 9, 2024

(54) SYSTEMS, METHODS, AND COMPUTER READABLE MEDIA FOR PROCESSING AND COMPOUNDING ULTRASOUND IMAGES IN THE PRESENCE OF MOTION

(71) Applicant: Covidien LP, Mansfield, MA (US)

(72) Inventors: Xiaofang Gan, Shanghai (CN); Wei Tan, Shanghai (CN)

(73) Assignee: Covidien LP, Mansfield, MA (US)

( * ) Notice: Subject to any disclaimer, the term of this patent is extended or adjusted under 35 U.S.C. 154(b) by 166 days.

(21) Appl. No.: 16/483,796

(22) PCT Filed: Feb. 10, 2017

(86) PCT No.: PCT/CN2017/073208
§ 371 (c)(1),
(2) Date: Aug. 6, 2019

(87) PCT Pub. No.: WO2018/145293
PCT Pub. Date: Aug. 16, 2018

(65) Prior Publication Data
US 2019/0369240 A1    Dec. 5, 2019

(51) Int. Cl.
*A61B 8/00* (2006.01)
*A61B 8/08* (2006.01)
(Continued)

(52) U.S. Cl.
CPC ........ *G01S 15/8995* (2013.01); *A61B 8/4461* (2013.01); *A61B 8/5253* (2013.01);
(Continued)

(58) Field of Classification Search
CPC ............. G01S 15/8995; G01S 7/52077; G01S 7/52085; G01S 7/4915; A61B 8/4461; A61B 8/5253; A61B 8/5276; A61B 8/54
See application file for complete search history.

(56) References Cited

U.S. PATENT DOCUMENTS

2006/0039589 A1* 2/2006 Hall ..................... A61B 8/08
382/128
2007/0014445 A1    1/2007 Lin
(Continued)

FOREIGN PATENT DOCUMENTS

CN      101199430 A     6/2008
CN      101527034 A     9/2009
(Continued)

OTHER PUBLICATIONS

International Search Report and Written Opinion of the International Searching Authority issued in corresponding Appl. No.: PCT/CN2017/073208 dated Nov. 23, 2017 (12 pages).
(Continued)

*Primary Examiner* — Patricia J Park

(74) *Attorney, Agent, or Firm* — Carter, DeLuca & Farrell LLP

(57) ABSTRACT

An ultrasound imaging method and system. The method comprises: for each of a plurality of steer angles, including a reference steer angle, transmitting acoustic energy to a target region at the particular steer angle, receiving acoustic reflections, and converting the acoustic reflections to an image, with the image being associated with the particular steer angle; computing motion information based on the image associated with the reference steer angle; and generating a compounded ultrasound image based on the image associated with each of the plurality of steer angles and based on the motion information.

8 Claims, 5 Drawing Sheets

(51) Int. Cl.
  *G01S 7/52* (2006.01)
  *G01S 15/89* (2006.01)
(52) U.S. Cl.
  CPC ........ *A61B 8/5276* (2013.01); *G01S 7/52077* (2013.01); *G01S 7/52085* (2013.01)

(56) References Cited

U.S. PATENT DOCUMENTS

| | | | |
|---|---|---|---|
| 2009/0264760 A1 | 10/2009 | Lazebnik et al. | |
| 2011/0054323 A1* | 3/2011 | Ahn | G01S 7/52085 600/443 |
| 2013/0128691 A1* | 5/2013 | Martins | G01S 15/8995 367/7 |
| 2013/0208965 A1 | 8/2013 | Sui et al. | |
| 2014/0187942 A1* | 7/2014 | Wang | A61B 8/0841 600/439 |
| 2016/0097845 A1* | 4/2016 | Chen | G01S 15/8995 367/7 |
| 2016/0140738 A1* | 5/2016 | Asaka | G01S 15/8952 382/131 |
| 2017/0049420 A1* | 2/2017 | Shikama | A61B 8/5276 |
| 2017/0301094 A1* | 10/2017 | Vignon | G06T 5/20 |
| 2020/0064468 A1* | 2/2020 | Holbek | G01S 15/8993 |

FOREIGN PATENT DOCUMENTS

| | | |
|---|---|---|
| CN | 101744639 A | 6/2010 |
| CN | 102487603 A | 6/2012 |
| CN | 102727255 A | 10/2012 |
| CN | 105433982 A | 3/2016 |

OTHER PUBLICATIONS

Office Action issued in corresponding Chinese Application No. 201780089025.5 dated Sep. 3, 2021, together with English language translation retrieved from the Global Dossier (17 pages).

* cited by examiner

SYSTEMS, METHODS, AND COMPUTER READABLE MEDIA FOR PROCESSING AND COMPOUNDING ULTRASOUND IMAGES IN THE PRESENCE OF MOTION

CROSS-REFERENCE TO RELATED APPLICATIONS

This application is a National Stage Application of PCT/CN2017/073208 under 35 USC § 371 (a), the disclosure of the above-identified application is hereby incorporated by reference in its entirety.

BACKGROUND

1. Technical Field

The present disclosure relates generally to ultrasound imaging, and more particularly to, systems, methods, and computer readable media for the processing and compounding of ultrasound images in the presence of motion.

2. Discussion of Related Art

An ultrasound system has become a popular diagnostic tool due to a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

The ultrasound system generally uses a probe containing a wide bandwidth transducer to transmit and receive ultrasound signals. When used with the human body, the ultrasound system forms images of human internal tissue by electrically exciting an acoustic transducer element or an array of acoustic transducer elements to generate ultrasound signals that travel into or through the body. The ultrasound signals produce ultrasound echo signals which are reflected from body tissue, which appear as discontinuities to the propagating ultrasound signals. Various ultrasound echo signals return to the transducer element and are converted into electrical signals, which are amplified and processed to produce ultrasound data for an image of the tissue.

The ultrasound system employs an ultrasound probe containing a transducer array for transmission and reception of ultrasound signals. The ultrasound system forms ultrasound images based on the received ultrasound signals. The technique of transmitting the ultrasound signals by steering the ultrasound beam at various angles has been used to obtain ultrasound images having more perspectives of a target region of interest.

Additionally, an ultrasound imaging system may include an ultrasound imaging unit and an image processing unit. The ultrasound imaging unit may control the transmission of ultrasound signals to a target region, such as tissue, and form data based on echo signals resulting from the transmitted ultrasound signals. The transmission of ultrasound signals at various steer angles may also be controlled by the ultrasound imaging unit. Using the echo signals, the ultrasound imaging unit and an image processing unit may generate a composite image of the target region, by combining the echoes at different steer angles using a technique known as spatial compounding. In some instances, the target region may move during the ultrasound procedure, adversely affecting the echo signals of one or more steer angles and causing deterioration in the compounded image of a target region. Accordingly, there is a need for systems and methods for determining motion of target regions during an ultrasound procedure and applying systems and methods for motion compensation for the compounded image of a target region.

SUMMARY

The present disclosure is directed to processing and compounding of ultrasound images in the presence of motion. In one aspect, an ultrasound imaging method operates, for each of a number of steer angles, including a reference steer angle (RSA), to transmit acoustic energy to a target region at a particular steer angle, receive acoustic reflections, and convert the acoustic reflections to an image, with the image being associated with the particular steer angle. The ultrasound imaging method computes motion information based on the image associated with the reference steer angle and generates a compounded ultrasound image based on the image associated with each of the steer angles and based on the motion information.

In one embodiment, generating the compounded ultrasound image includes, for each of the steer angles, applying a particular weighting to the image associated with the particular steer angle to generate a weighted image associated with the particular steer angle, where the particular weighting is based on the motion information, and combining the weighted images associated with the steer angles to generate the compounded ultrasound image.

In a further embodiment, the image associated with each steer angle has an H by W array of pixels, where H is a height of the image in number of pixels and W is a width of the image in number of pixels, and where each pixel has a pixel value. In one embodiment, computing the motion information includes computing a difference between a preexisting image and the image associated with the reference steer angle (RSA) to generate a difference image, and filtering the difference image using a low pass filter to generate a filtered difference image having pixels $Dis(i,j)$.

In one aspect, the disclosed ultrasound imaging method operates, for each of the steer angles other than the reference steer angle, to compute a weight for each pixel of the image associated with the particular steer angle, where the steer angles include a number N of steer angles designated as $1 \leq k \leq N$, and where the weight for each pixel $(i,j)$ of the image associated the particular steer angle k is computed by:

$$W_{k,k \neq rsa}(i,j) = C_{k,k \neq rsa} \cdot f(Dis(i,j)), \text{ if } Dis(i,j) \leq TH$$

$$W_{k,k \neq rsa}(i,j) = 0, \text{ if } Dis(i,j) > TH$$

where:
$f$ is a function that inverts pixel values such that $f(Dis(i,j))$ is smaller as $Dis(i,j)$ is larger,
$C_k$ are predetermined values where $C_k$ is smaller as the steer angle is larger and where $\Sigma_{k=1}^{N} C_k = 1$, and
TH is a predetermined threshold value.

In yet another embodiment, generating the compounded ultrasound image includes computing, for each pixel $(i,j)$:

$$\text{Compounded image }(i, j) = \sum_{k=1}^{N} W_k(i, j) \cdot \text{Image}_k(i, j)$$

where $\text{Image}_k$ is the image associated with steer angle k, and where:

$$W_{k,k=rsa}(i,j) = 1 - \Sigma_{k=1,k\neq rsa}^{N} W_k(j,k), \text{ if } Dis(i,j) \leq TH$$

$$W_{k,k=rsa}(i,j) = 1, \text{ if } Dis(i,j) > TH.$$

In another embodiment, the reference steer angle is zero degrees, which is the steer angle corresponding to transmitting acoustic energy from all transducer elements at the same time. In one embodiment, the motion information is computed based further on a previously compounded ultrasound image.

In accordance with at least one aspect of the disclosure, the ultrasound system includes a transducer configured to, for each of a number of steer angles, including a reference steer angle, transmit acoustic energy to a target region at a particular of steer angle, receive acoustic reflections, and convert the acoustic reflections to Radio Frequency (RF) data. The ultrasound system further includes front-end circuitry configured, for each of the steer angles, to process the RF data associated with the particular steer angle to generate an image associated with the particular steer angle, and a computing device configured to generate motion information based on the image associated with the reference steer angle and generate a compounded ultrasound image based on the motion information and the image associated with each of the steer angles.

In still a further embodiment of the ultrasound system, generating the compounded ultrasound image includes applying, for each of the steer angles, a particular weighting to the image associated with the particular steer angle to generate a weighted image associated with the particular steer angle, where the particular weighting is based on the motion information, and combining the weighted images associated with the steer angles to generate the compounded ultrasound image.

In another embodiment of the ultrasound system, the image associated with each particular steer angle has an H by W array of pixels, where H is a height of the image in number of pixels and W is a width of the image in number of pixels, and where each pixel has a pixel value. In one embodiment, generating the motion information includes computing a difference between a preexisting image and the image associated with the reference steer angle (RSA) to generate a difference image, and filtering the difference image using a low pass filter to generate a filtered difference image having pixels Dis(i,j).

In one aspect of the ultrasound system, the computing device is further configured, for each of the steer angles other than the RSA, to compute a weight for each pixel of the image associated with the particular steer angle, where the steer angles include a number N of steer angles designated as $1 \leq k \leq N$, and where the weight for each pixel (i,j) of the image associated the particular steer angle k is computed by:

$$W_{k,k\neq rsa}(i,j) = C_{k,k\neq rsa} \cdot f(Dis(i,j)), \text{ if } Dis(i,j) \leq TH$$

$$W_{k,k\neq rsa}(i,j) = 0, \text{ if } Dis(i,j) > TH$$

where:
$f$ is a function that inverts pixel values such that $f(Dis(i,j))$ is smaller as $Dis(i,j)$ is larger,
$C_k$ are predetermined values where $C_k$ is smaller as the steer angle is larger and where $\Sigma_{k=1}^{N} C_k = 1$, and
TH is a predetermined threshold value.

In still a further embodiment of the ultrasound system, generating the compounded ultrasound image includes computing, for each pixel (i,j):

$$\text{Compounded image }(i,j) = \sum_{k=1}^{N} W_k(i,j) \cdot \text{Image}_k(i,j)$$

where $\text{Image}_k$ is the image associated with steer angle k, and where:

$$W_{k,k=rsa}(i,j) = 1 - \sum_{k=1,k\neq rsa}^{N} W_k(i,j), \text{ if } Dis(i,j) \leq TH$$

$$W_{k,k=rsa}(i,j) = 1, \text{ if } Dis(i,j) > TH$$

In one embodiment of the ultrasound system, the reference steer angle is zero degrees, which is the steer angle corresponding to transmitting acoustic energy from all transducer elements at the same time. In one embodiment, the motion information is computed based further on a previously compounded ultrasound image.

The Summary is provided to introduce the present disclosure in a condensed form. This Summary does not relate to key or essential features and does not define or limit the scope of the present disclosure in any way.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

The present disclosure relates to performing spatial compounding using motion information to reduce blurring. Spatial compounding is an ultrasound imaging technique that obtains images of a target region by directing ultrasound wave to a target region at different angles, and then combining the images resulting from each angle. Spatial compounding can produce an image with better quality than imaging a target region at only one angle. Difficulties arise in spatial compounding, however, when a target region is susceptible to motion, such as when imaging a heart, lungs, or a fetus. In such cases, spatial compound can result in images with excessive blurring.

An ultrasound probe is an electronic, reusable device having an array of transducer elements capable of precise waveform timing and intricate waveform shaping and capable of communicating analog or digitized data to an imaging system. By utilizing independent transducer elements aimed at a target region at various angles and processing the information obtained by the independent transducer elements, the imaging system is capable of generating plurality of ultrasound images which may be combined to generate a single ultrasound image which can produce an image of the target region with higher quality than a single uncombined ultrasound image. As discussed in further detail below, various embodiments of an ultrasound imaging system are provided with respect to spatial compounding in the presence of motion.

Figure 1:
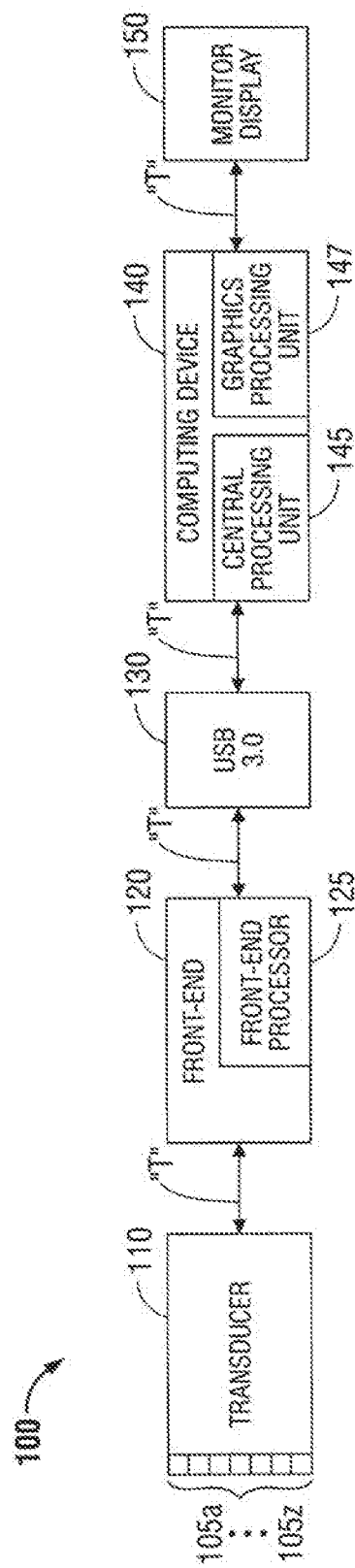
FIG. 1 illustrates a top level architecture of one embodiment of an ultrasound imaging system, in accordance with aspects of the present disclosure.

FIG. 1 illustrates a block diagram of an ultrasound imaging system 100 in accordance with an embodiment of the present disclosure. Ultrasound imaging system 100 includes a transducer unit 110 containing a transducer array 105 including transducer elements 105a-z, front-end circuitry 120, a communication interface 130, a computing device 140, and a display 150. Transducer unit 110 is a device that converts acoustic energy/acoustic waves into electrical signals and converts electrical signals into acoustic energy/acoustic waves. As used herein, the term "acoustic" includes waves having audible frequencies (i.e., below 20 kHz) and waves having ultrasonic frequencies (i.e., above 20 kHz). The transducer unit 110 includes an array of transducer elements 105a-z, which transmit the ultrasound waves toward a target region at specific and/or predetermined angles referred to as "steer angles." Ultrasound waves propagate omnidirectionally in the absence of waveguides. When all of the transducer elements 105a-z activate at the same time, the ultrasound waves created by all of the transducer elements 105 propagate away from the transducer elements at the same time. This is referred to as zero degree steer angle. Each transducer element 105a-z, however, can be individually controlled, and by activating particular transducer elements at different times, the transducer unit can adjust the steer angle of the ultrasound transmission without physically moving the transducer unit. The waves from the earlier activations will have travelled some distance when the waves from the later activations are first propagated, thereby forming a wave front that appears at an angle relative to the transducer unit 110. Thus, the steer angle can be electronically adjusted using transducer timing, without physically moving the transducer unit 110.

The transducer array 105 receives ultrasound waves that are reflected or echoed from the target region, and transducer unit 110 converts the received ultrasound waves to electrical signals. Electrical signals converted by transducer unit 110 may be in the form of radio frequency (RF) signals. As shown in FIG. 1, transducer unit 110 is interfaced with or coupled to front-end circuitry 120 via communication line "T." As used herein, communication lines "T" denote lines that are capable of communicating RF data, image data, or other electrical signals, and that provide an interface between the components of ultrasound imaging system 100.

Referring now to front-end circuitry 120, front-end circuitry 120 includes a receiver (not shown) that receives RF signals from transducer unit 110, a transmitter (not shown) that transmits RF signals to transducer unit 110, and a front end processor 125. Front-end circuitry 120 performs specific processing of the RF signals as described below. Front-end processor 125 can utilize specific ultrasound waveforms, beam patterns, receiver filtering techniques, amplification, and demodulation schemes, for imaging. Front-end circuitry 120 also converts digital signals to analog signals and vice versa. Front-end circuitry 120 interfaces with and is coupled to transducer unit 110 via transmission line "T" and also interfaces with computing device 140 via transmission lines "T" and a communication interface 130. Communication interface 130 is an interfacing device that allows front-end circuitry 120 to communicate with the computing device 140 and may include a Universal Serial Bus (USB), such as USB 3.0, or other bus interfaces or protocols capable of interfacing with computers and electronic devices.

In the illustrated embodiment, computing device 140 includes a central processing unit (CPU) 145 and a graphics processing unit (GPU) 147. Central processing unit 145 and GPU 147 provide image processing and post-processing of information received from the front-end circuitry 120, and can control or direct other operations. In some embodiments, computing device 140 may be a personal computer or a laptop or other computing device.

In some embodiments, transducer unit 110 and front-end circuitry 120 are contained within a single device, which interfaces with computing device 140 via communication interface 130. In other embodiments, transducer unit 110 and front-end circuitry 120 are contained in separate devices. In one embodiment, the communication interface 130, the computing device 140 and/or the display 150 can be contained within one device. In another embodiment, the computing device 140 and the display 150 can be separate devices. Other configurations are contemplated to be within the scope of the present disclosure.

Figure 2:
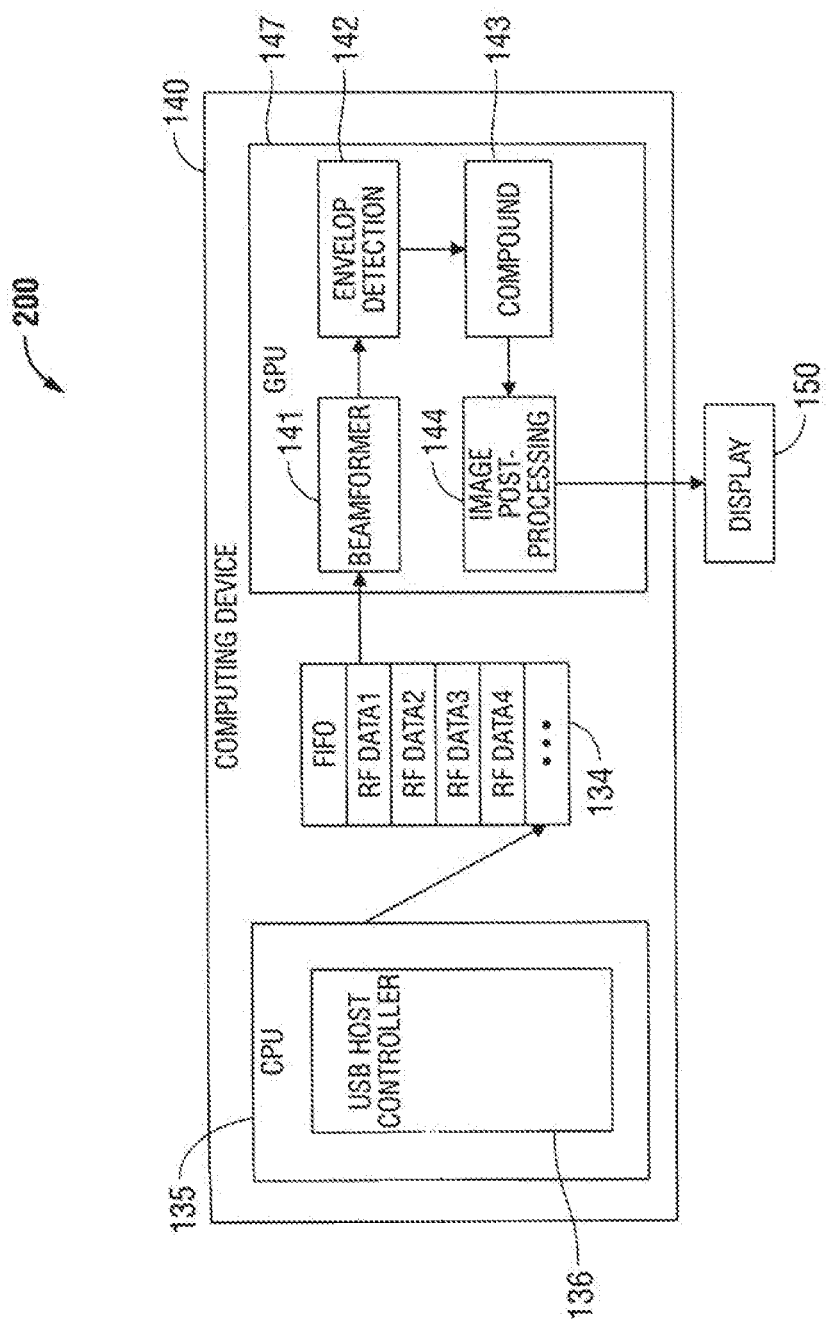
FIG. 2 illustrates one embodiment of an imaging system of an ultrasound imaging system, in accordance with aspects of the present disclosure.

Referring now to FIG. 2, a block diagram of an imaging system 200 which includes computing device 140 and a display 150 is illustrated. System 200 is utilized to generate compounded images. System 200 communicates with the transducer unit and/or front end circuitry (FIG. 1, 110, 120) to receive RF/image data and performs processing on the RF/image data to generate compounded images. Computing device 140 includes CPU 145, First-In First-Out (FIFO) buffer 134, GPU 147, and may include a display 150. In other embodiments, display 150 may, for example, be a separate monitor outside of computing device 140. CPU 145 is capable of functioning as, at least, a USB host controller 136. GPU 147 is capable of handling operations such as beamforming, envelope detection, image compounding, and image post-processing, which are performed by beamforming unit 141, envelop detection unit 142, compounding unit 143, and image post-processing unit 144, respectively. As used herein, the term "beamforming" shall refer to receive beamforming, unless usage or context indicates that transmit beamforming or another meaning is intended in any particular instance.

CPU 145 controls the USB host controller 136 to receive the RF/image data from the transducer unit and/or the front end circuitry. When the RF/image data is received, CPU 145 transmits and writes the RF/image data to FIFO buffer 134. The RF/image data in FIFO buffer 134 is next processed by GPU 147 in the order which it was received, such that the first RF/image data received is processed first. FIFO buffer 134 is coupled with CPU 145 and GPU 147. CPU 145 stores each RF/image data in FIFO buffer 134 as long as the FIFO buffer 135 has available memory space.

Figure 3:
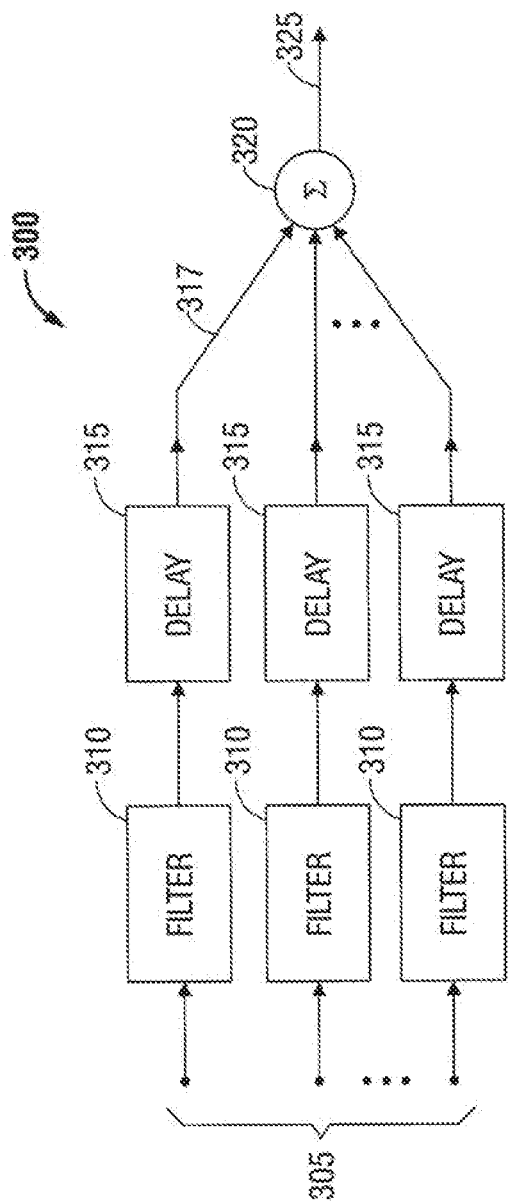
FIG. 3 illustrates a block diagram of one embodiment of the operations of a beamforming unit, in accordance with aspects of the present disclosure.

Turning now to GPU 147, beamforming unit 141 performs processing of RF/image data by delaying certain signals received by particular transducer elements 105a-z, to compensate for certain transducer elements being farther away from the target region than other transducer elements, in order to temporally align the signals received by the individual transducer elements 105a-z. After the signals of the various transducer elements are aligned, beamforming unit 141 combines the data from the various transducer elements to generate RF/image data for a single image, as illustrated in FIG. 3. Envelope detection unit 142 is configured to detect the envelope of the signals generated by beamforming unit 141, thus removing the carrier signal. Envelope detection unit 142 is used to detect the peaks in the received RF/image data, and log compression is used to reduce the dynamic range of the received RF/image data. Compounding unit 143 is utilized to analyze whether there is motion present in the received RF/image data which may affect the compounded images, to correct for the motion, and to combine the images generated by beamforming unit 141. Following the compounding process by compounding unit 143, a compounded ultrasound image is generated. Image post-processing unit 144 is configured to automatically enhance the generated ultrasound image for a medical professional or technician. The medical professional or technical may control the amount the generated compounded image is post-processed. The resulting image may then be displayed on a screen of the display 150.

FIG. 2 is merely exemplary and in various embodiments, the operations described in connection with FIG. 2 can be handled by other configurations of processor(s), software, programmable logic devices, integrated circuits, ASICs, circuitry, and/or hardware. For example, in certain embodiments, the CPU or a microprocessor or a digital signal processor can handle some or all of the operations. In certain embodiments, some or all of the operations can be performed by hardware or circuitry, such as the beamforming and envelope detection operations. Other configurations not specifically disclosed herein are contemplated to be within the scope of the disclosed technology.

Referring now to FIG. 3, FIG. 3 illustrates a block diagram 300 of an example of beamforming, including filtering, time delaying, and summing as RF/image data is processed by beamforming unit 141 of GPU 147. As shown in FIG. 3, RF/image data 305 represents data produced by transducer elements 105a-z and is read from FIFO buffer 134. RF/image data 305 is filtered via filters 310 in order to reduce noise, and filters 310 may be in the form of finite impulse response filters, infinite impulse response filters or median filters, as each is understood by those skilled in the art. The filtered data is delayed by time delay units 315, which generate output data 317 corresponding to RF/image data 305. As described above, beamforming unit 141 uses temporal delays to compensate for certain transducer elements 105a-z being farther away from the target region than other transducer elements 105a-z, in order to temporally align the signals received by the individual transducer elements 105a-z. For example, as ultrasound reflections are received by transducer unit 110, transducer elements 105a-z closer to the target region will receive the reflections before transducer elements 105a-z that are farther away from the target region. Thus, transducer elements 105a-z will not all receive the reflections at the same time. The temporal delays operate to align RF/image data 305 from transducer elements 105a-z in time. After the signals of transducer elements 105a-z are aligned, summing unit 320 combines all output data 317 and generates beamformed output data 325, for a particular steer angle. Each beamformed output data 325 is a separate image having a matrix of pixels that is H-pixels high and W-pixels wide, for a particular steer angle.

Referring again to beamforming unit 141 of FIG. 2 and block diagram 300 of FIG. 3, beamforming unit 141 may be implemented by a programmable logic device. The programmable logic device filters, interpolates, demodulates, phases, applies apodization, delays and/or sums the received signals, which are operations of beamforming unit 141. The programmable logic device controls the delays and characteristics of ultrasound waveforms, and generates ultrasound waveforms from memory. The programmable logic device may also implement relative delays between the waveforms as well as filter, interpolate, modulate, phase, and apply apodization. The programmable logic device can control beamforming unit 141 to perform functions to process the plurality of signals associated with multi-element electrically scanned transducer arrays.

Figure 4:
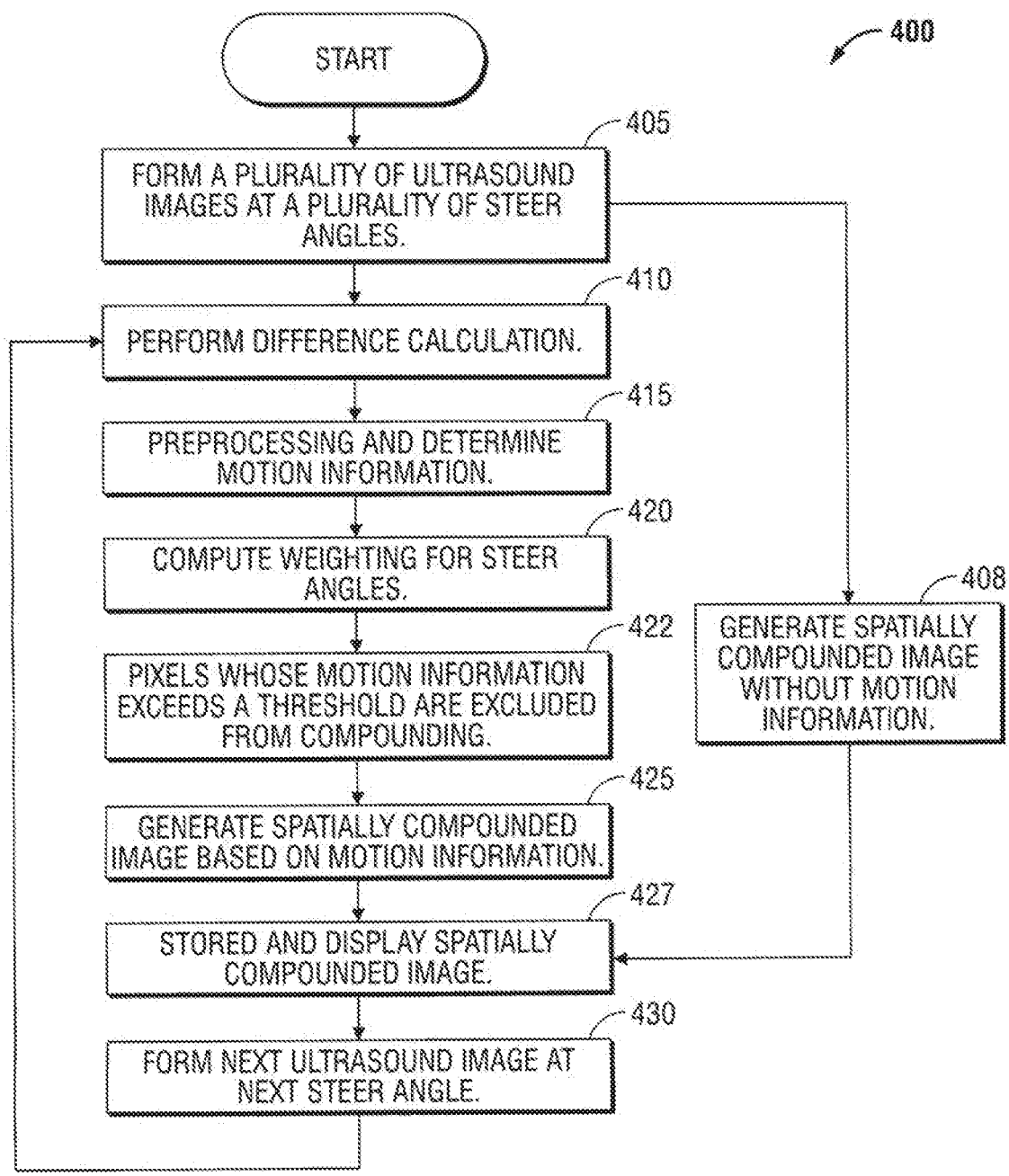
FIG. 4 illustrates a flow diagram of one embodiment of a spatial compounding method, in accordance with aspects of the present disclosure.

Referring now to FIG. 4, a flowchart of one embodiment of a method 400 for spatial compounding is illustrated. The flowchart begins at step 405, where a plurality of ultrasound images at a plurality of steer angles are formed. As described in the detail descriptions of FIGS. 2 and 3, beamforming unit 141 of FIG. 2 is utilized to generate the beamformed output data 325 of FIG. 3. Each beamformed output data 325 is a different ultrasound image at a different steer angle. There can be a number N of different steer angles, and one of the steer angles is designated as a reference steer angle (RSA). In one embodiment, the RSA can be the zero degree steer angle. In another embodiment, the RSA can be a non-zero degree steer angle. The ultrasound images at different steer angles include H-by-W matrices of pixels, where H denotes image height in number of pixels and W denotes image width in number of pixels. At step 405, the N ultrasound images at the N different steer angles are formed.

In one embodiment, the method 400 can proceed to step 408 and generate a spatially compounded image without using any motion information, as is known in the art, and then at step 427, store and display the spatially compounded image. In another embodiment, the method 400 can proceed to steps 410-425 to compute motion information and generate a spatially compounded image based on the motion information, as described below.

Step 410 requires a stored preexisting image to be available for purposes of a difference calculation used to generate information about motion at a target region. The stored, preexisting image serves as a base image where differences from the base image are viewed as being motion. If, after step 405, a stored preexisting image is not available for the difference calculation, method 400 can proceed to step 408 instead. For example, for the first iteration of the spatial compounding operation, the method 400 can proceed to step 408. In the second iteration of the spatial compounding operation where the compounded image from the first iteration would be available to serve as a base image, the method 400 can proceed to step 410. In the second iteration, the compounded image from the first iteration would be used for the difference calculation in the second iteration at step 410.

At step 410, a stored image is selected and the ultrasound image with the RSA is selected, and a difference calculation is performed between the two selected images. In one embodiment, the stored image can be a preexisting, previously compounded image. In one embodiment, the stored image can be a preexisting ultrasound image associated with a steer angle other than the RSA.

The difference calculation is performed between each pixel coordinate (i,j) of the stored, preexisting image and the corresponding pixel coordinate (i,j) of the ultrasound image at the reference steer angle, based on equation (1) below, where (i,j) denotes a pixel coordinate and where $1 \leq i \leq H$ and $1 \leq j \leq W$.

$$\text{Difference image}(i,j) = |\text{Preexisting image}(i,j) - \text{Reference steer angle image}(i,j)| \qquad (1)$$

At step 415, preprocessing is performed on the difference image. In one embodiment, the difference image computed based on equation (1) above is filtered. The resulting filtered difference image is denoted as Dis, and each pixel therein is denoted as Dis(i,j). In one embodiment, the filter can be a low pass filter that reduces noise in the difference image, such as a a 5*5 median filter or a Gaussian smoothing filter. Other filters are contemplated to be within the scope of the present disclosure. This filtered difference image provides an indication of motion of the target region during imaging and serves as motion information. In one embodiment, the difference image does not need to be filtered and itself serves as the motion information. The difference calculation of equation (1) is exemplary. Other ways of determining motion information are contemplated to be within the scope of the present disclosure.

Next, at step 420, a weight matrix is generated for each ultrasound image at each non-rsa based on equations (2)-(7) below:

$$W_{k,k \neq rsa}(i,j) = C_{k,k \neq rsa} * f(Dis(i,j)) \quad (2)$$

where k is the steer angle ID and $1 \leq k \leq N$, and where N is the number of steer angles, and rsa is the reference steer angle. The coefficient $C_k$ is a predetermined coefficient associated with steer angle k. The function $f(Dis(i,j))$ is a function applied to each pixel coordinate (i,j) of the filtered difference image. $C_k$ serves as a steer angle-specific coefficient applicable to every pixel of the image associated with steer angle k, and $f(Dis(i,j))$ serves as a pixel-specific weight applicable to pixel coordinate (i,j) in the ultrasound images of every steer angle. Thus, equation (2) computes a weight $W_{k,k \neq rsa}(i,j)$ for steer angle k and pixel coordinate (i,j) using an angle-specific coefficient and a pixel-specific weight. In one embodiment, $C_k$ becomes larger as the steer angle approaches the RSA:

$$P_k = 1 - \frac{|k - rsa|}{N} \quad (3)$$

$$C_k = P_k \Big/ \sum_{1}^{N} P_k \quad (4)$$

$$\sum_{k=1}^{N} C_k = 1 \quad (5)$$

Equation (3) generates an intermediate variable $P_k$, which decreases as the steer angle k diverges from the rsa and is largest (equal to 1) when the steer angle is the rsa. Equation (4) generates $C_k$ and is used to normalize the values of $C_k$ so that the sum of $C_k$ across all steer angles k is 1, as shown in equation (5). In other words, as the steer angle diverges from the RSA, the weight given to each pixel coordinate (i,j) at that specific steer angle is decreased.

In one embodiment, $f(Dis(i,j))$ has an inverse relationship with Dis(i,j), such that $f(Dis(i,j))$ decreases in value as Dis(i,j) increases in value. In this manner, $W_{k,k \neq rsa}(i,j)$ generally decreases in value as Dis(i,j) increases in value, for a particular steer angle k. Thus, pixels that reflect greater motion are more lightly weighted for spatial compounding, and pixels that reflect lesser motion or no motion are more heavily weighted for spatial compounding.

Next, at step 422, pixel coordinates (i,j) whose motion information Dis(i,j) exceeds a predetermined threshold for Dis(i, j) are excluded from the compounding process. Where a pixel coordinate (i,j) has a Dis(i,j) value that exceeds the predetermined threshold for Dis(i,j), it is determined that motion of the ultrasound image at or around pixel coordinate (i,j) exceeds acceptable movement for compounding, and therefore, compounding the ultrasound image at those pixel coordinates (i,j) would not produce an image of the target region with sufficient quality. An example of such a threshold value (TH) is shown in equation (6):

$$TH = f_1(f_s) \quad (6)$$

where $f_s$ is the frame rate of the ultrasound imaging system, and $f_1$ is a function that inverts $f_s$ such that $f_1(f_s)$ is smaller as $f_s$ is larger. For example, the threshold value can be $TH = a + b/f_s$, where a and b are constants.

In such a situation where a pixel coordinate is excluded from the compounding process, the weights $W_{k,k \neq rsa}(i,j)$ assigned to the pixel coordinate (i,j) of every non-reference steer angle k is set to the rsa, and the weight $W_{k=rsa}(i,j)$ assigned to the pixel coordinate (i,j) of the reference steer angle rsa is set to 1, as shown in equation (7):

$$W_{k,k \neq rsa}(i,j) = 0 \text{ and } W_{rsa}(i,j) = 1 - \sum_{k=1, k \neq rsa}^{N} W_k(i,j) = 1 \quad (7)$$

The weight metric $W_k(i,j)$ at pixel coordinate (i,j) and steer angle k is included in a weight table $W_k$, which is utilized during spatial compounding of step 425. At step 425, spatial compounding is performed, as described in further detail in the description of FIG. 5, and a spatially compounded image is generated and stored in memory. Next, at step 427, the spatially compounded image is stored and displayed. The weighting technique of equations (2)-(7) is exemplary. Other weighting approaches are contemplated to be within the scope of the present disclosure.

Next, method 400 proceeds to step 430 and generates a new ultrasound image at another steer angle. Next, method 400 returns to step 410 where the difference calculation is computed using the previously compounded image from step 425, and the motion information is determined at step 415. As described in more detail below in the description of FIG. 5, steps 420-425 then operate to generate a new spatially compounded image using the motion information determined at step 415 and the new ultrasound image previously formed at step 430.

Thus, spatial compounding is performed using all images at various steer angles, but those images which have pixels with higher weights have a greater effect on the final compounded image than those images which have pixels with lower weights. Furthermore, in generating the spatially compounded image, static portions of images will be compounded with a larger weight than portions of images with motion, thereby decreasing motion blurring for the final spatially compounded image. The flow of operations in FIG. 4 is exemplary and, unless indicated otherwise, the operations can be performed in a different order and/or can be performed in parallel.

Figure 5:
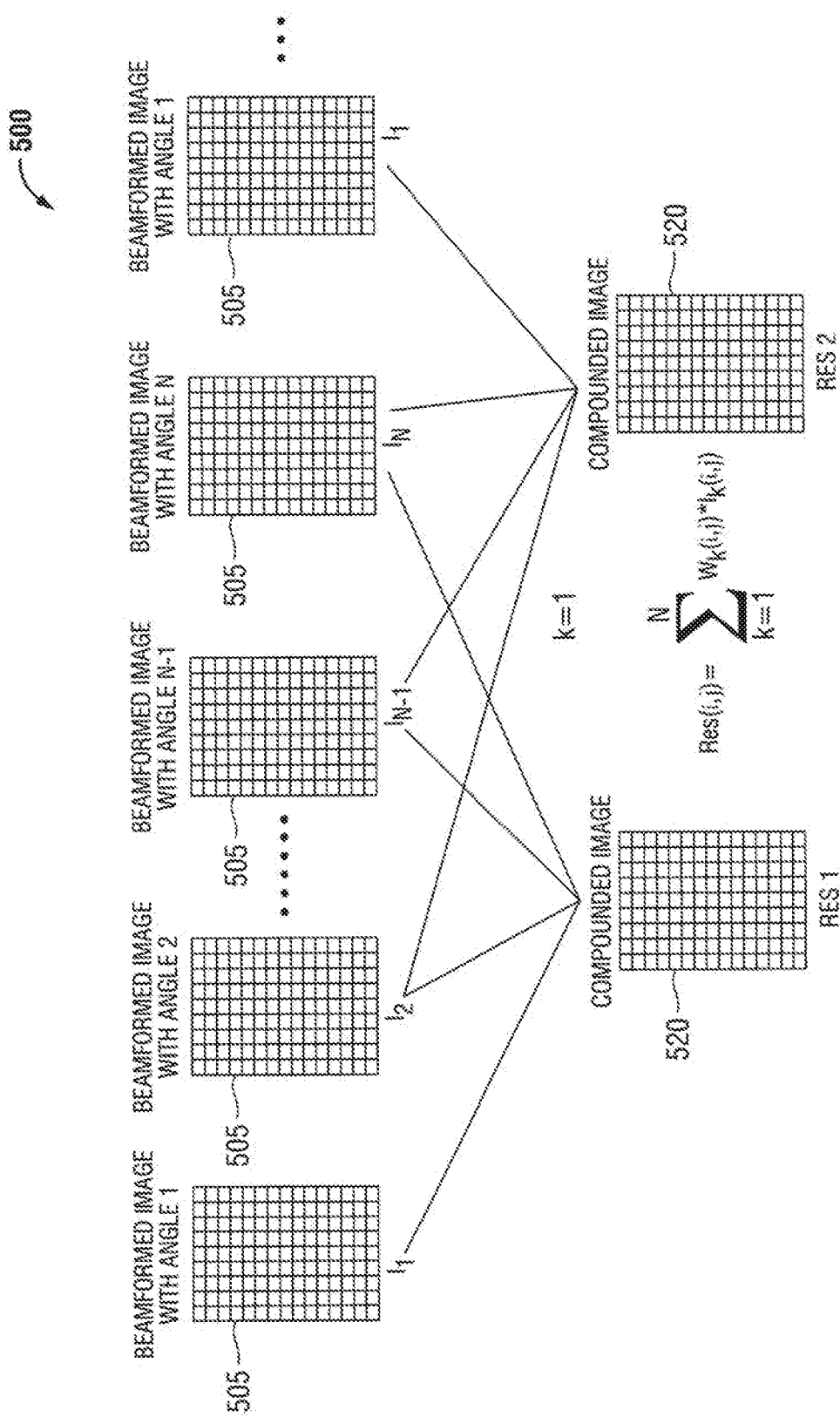
FIG. 5 illustrates the spatial compounding method of FIG. 4, as applied to a plurality of ultrasound images, in accordance with aspects of the present disclosure.

Referring now to FIG. 5, a diagram 500 illustrating the spatial compounding of step 425 of FIG. 4 is provided. As illustrated in FIG. 5, a plurality of images 505 ($I_1$-$I_N$) associated with different steer angles 1 through N are shown as a plurality of H-by-W pixel matrices. Motion information and weighting for each of the steer angles are computed as described above with respect to steps 410-422 of FIG. 4. In step 425 of FIG. 4, images 505 ($I_1$-$I_N$) are weighted and combined to form a spatially compounded image denoted as Res, according to equation (8):

$$Res(i, j) = \sum_{k=1}^{N} W_k(i, j) * I_k(i, j) \quad (8)$$

where Res(i,j) corresponds to pixel coordinate (i,j) in the compounded image 520, generated from the spatial compounding of the plurality of images 505 ($I_1$-$I_N$), with each weight table $W_k$(i,j) being applied to the pixels of corresponding image $I_k$. The weight tables $W_k$(i,j) are determined at steps 420-422 in FIG. 4. The spatially compounded image Res1 is stored and displayed.

FIG. 5 also illustrates step 430 of FIG. 4, which generates a new ultrasound image for another steer angle. As shown in FIG. 5, compounded image 520 (Res1) corresponds to a compounding of plurality of images 505 ($I_1$-$I_N$). When a new ultrasound image $I_{1'}$ becomes available (step 430 in FIG. 4), it replaces image $I_1$ and a new compounded image 520 (Res2) is generated using the new image $I_{1'}$ by compounding the plurality of images 505 ($I_2$-$I_N$ and $I_{1'}$) (step 425 of FIG. 4).

The disclosed system sequentially generates ultrasound images at steer angles 1 through N. After the ultrasound image at steer angle N is generated, the system cycles back to steer angle 1 and repeats. Each image I includes all RF/image data 305 from all of transducer elements 105a-z of transducer array 105, for a particular steer angle. Initially, the first spatially compounded image is generated based on the images $I_1$ through $I_N$. When the system cycles back to steer angle 1 again, a new image $I_{1'}$ replaces the first image $I_1$. When viewed in time, the "window" for spatial compounding changes from using images $I_1$ through $I_N$, to using images $I_2$ through $I_N$ and $I_{1'}$. Persons skilled in the art will recognize this methodology to be what is known as a "sliding window" technique. In the next iteration, the system generates a new image $I_{2'}$ at steer angle 2, and the new image $I_{2'}$ replaces the first image $I_2$. Then, when viewed in time, the window for spatial compounding changes from using images $I_2$ through $I_{1'}$, to using images $I_3$ through $I_N$ and $I_{1'}$ and $I_{2'}$. ($I_{1'}$ and $I_{2'}$ replace $I_1$ and $I_2$, respectively, and therefore for compounding purposes an N number of steer angles is always utilized during compounding). Thus, as the steer angle of transducer unit 110 is changed and swept through angles 1-N, compounding and display operations of imaging system 200 continually compounds and updates the display of the compounded image by removing a previous image and including one new image of the same steer angle. In this manner, the initial latency for generating and displaying the first spatially compounded image Res1 is N beamforming time periods, but the latency thereafter for generating and displaying another spatially compounded image Res2 shortens to one beamforming time period, thereby increasing the display frame rate of the ultrasound imaging. Based on the aforementioned systems, methods, and devices, spatial compounding of images for a target region that is moving is completed with greater clarity through the use of the imaging and ultrasound device and methods disclosed and described herein. The spatial compounding operation of FIG. 5 is exemplary and variations are contemplated to be within the scope of the present disclosure. For example, spatial compounding does not need to be performed every time a new ultrasound image is available. For example, spatial compounding can be performed for every two new ultrasound images, or at another frequency or interval. Similarly, motion information does not need to be generated every time a new ultrasound image is available and can be generated at another frequency or interval.

A computer or computing device may be incorporated within one or more ultrasound imaging system or one or more electronic devices or servers to operate one or more processors to run the ultrasound imaging system. It is to be understood, therefore, that this disclosure is not limited to the particular forms illustrated and that it is intended in the appended claims to embrace all alternatives, modifications, and variations which do not depart from the spirit and scope of the embodiments described herein. Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure.

The detailed description is provided with reference to the accompanying drawings. One of ordinary skill in the art will recognize that the description is illustrative only and is not in any way limiting. Other embodiments of the present disclosure will be understood by persons skilled in the art, having the benefit of this disclosure, as being within the scope of the disclosed technology. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:
1. An ultrasound imaging method comprising:
for each of a plurality of steer angles including a reference steer angle, generating an ultrasound image of a target region;
computing a difference between each pixel coordinate of the ultrasound image generated for the reference steer angle and each corresponding pixel coordinate of the ultrasound images generated for the steer angles other than the reference steer angle;
generating a difference image based on the computed difference;
computing, for each pixel coordinate of each ultrasound image generated for the steer angles other than the reference steer angle, motion information of the target region based on the difference image;
for each ultrasound image generated for the steer angles other than the reference steer angle, generating a weighted ultrasound image by assigning a weight to each pixel coordinate of the ultrasound image;
for each weighted ultrasound image, excluding each pixel coordinate from the weighted ultrasound image whose motion information exceeds a predetermined threshold without discarding the weighted ultrasound image;
combining the weighted ultrasound images to generate and display an initial compounded ultrasound image of the target region; and replacing a previous ultrasound image generated for a first steer angle of the plurality of steer angles with a subsequent ultrasound image generated corresponding to the first steer angle to compound and update the initial compounded ultrasound image such that a first latency for generating and displaying the initial compounded ultrasound image includes a plurality of beamforming periods and a second latency for generating and displaying another compounded ultrasound image subsequent to the initial compounded ultrasound image is reduced to one beamforming period.

2. The method according to claim 1, wherein each of the ultrasound images comprises an H by W array of pixels, wherein H is a height of the image in number of pixels and W is a width of the image in number of pixels, and wherein each pixel has a pixel value.

3. The method according to claim 1, wherein computing the motion information further comprises filtering the difference image using a low pass filter to generate a filtered difference image.

4. The method according to claim 1, wherein generating the compounded ultrasound image includes performing envelope detection, compounding, and post-processing by a graphics processing unit.

5. An ultrasound system comprising:
a transducer configured to, for each of a plurality of steer angles, including a reference steer angle:
transmit acoustic energy to a target region at a particular steer angle;
receive acoustic reflections; and
convert the acoustic reflections to Radio Frequency (RF) data;
a front-end circuitry configured, for each of the plurality of steer angles, to process the RF data associated with the particular steer angle to generate an image of the target region;
one or more processors; and
one or more processor-readable storage media storing instructions which, when executed by the one or more processors, cause performance of:
computing a difference between each pixel coordinate of the image generated for the reference steer angle and each corresponding pixel coordinate of the images generated for the steer angles other than the reference steer angle;
generating a difference image based on the computed difference;
generating, for each pixel coordinate of each image generated for the steer angles other than the reference steer angle, motion information of the target region based on the difference image;
for each image generated for the steer angles other than the reference steer angle, generating a weighted image by assigning a weight to each pixel coordinate of the image;
for each weighted image, excluding each pixel coordinate from the weighted image whose motion information exceeds a predetermined threshold without discarding the weighted image;
combining the weighted images to generate an initial compounded ultrasound image of the target region; and
replacing a previous ultrasound image generated for a first steer angle of the plurality of steer angles with a subsequent ultrasound image generated corresponding to the first steer angle to compound and update the initial compounded ultrasound image such that a first latency for generating and displaying the initial compounded ultrasound image includes a plurality of beamforming periods and a second latency for generating and displaying another compounded ultrasound image subsequent to the initial compounded ultrasound image is reduced to one beamforming period.

6. The system according to claim 5, wherein each of the ultrasound images comprises an H by W array of pixels, wherein H is a height of the image in number of pixels and W is a width of the image in number of pixels, and wherein each pixel has a pixel value.

7. The system according to claim 5, wherein generating the motion information further comprises:
filtering the difference image using a low pass filter to generate a filtered difference image.

8. A system, comprising:
one or more processors; and
one or more non-transitory processor-readable storage media storing instructions which, when executed by the one or more processors, cause performance of:
receiving, from an ultrasound transducer, an ultrasound image for each steer angle of a plurality of steer angles of the ultrasound transducer, the plurality of steer angles including a reference steer angle;
computing a difference between each pixel coordinate of the ultrasound image generated for the reference steer angle and each corresponding pixel coordinate of each ultrasound image received for each steer angle other than the reference steer angle;
generating a difference image based on the computed difference;
computing, for each pixel coordinate of each ultrasound image received for each steer angle other than the reference steer angle, motion information of a target region based on the difference image;
for each ultrasound image received for each steer angle other than the reference steer angle, generating a weighted ultrasound image by assigning a weight to each pixel coordinate of each received ultrasound image;
for each weighted ultrasound image, excluding each pixel coordinate from the weighted ultrasound image whose motion information exceeds a predetermined threshold without discarding the weighted ultrasound image;
combining the weighted ultrasound images to generate and display an initial compounded ultrasound image of the target region; and
replacing a previous ultrasound image received for a first steer angle of the plurality of steer angles with a subsequent ultrasound image received corresponding to the first steer angle to compound and update the initial compounded ultrasound image such that a first latency for generating and displaying the initial compounded ultrasound image includes a plurality of beamforming periods and a second latency for generating and displaying another compounded ultrasound image subsequent to the initial compounded ultrasound image is reduced to one beamforming period.

* * * * *